United States Patent [19]
Knisley

[11] Patent Number: 5,824,028
[45] Date of Patent: Oct. 20, 1998

[54] LINE ELECTRODE ORIENTED RELATIVE TO FIBER DIRECTION

[75] Inventor: Stephen B. Knisley, Vestavia Hills, Ala.

[73] Assignee: The UAB Research Foundation, Birmingham, Ala.

[21] Appl. No.: 717,416

[22] Filed: Sep. 20, 1996

[51] Int. Cl.⁶ .................................. A61N 1/00; A61B 5/04
[52] U.S. Cl. ........................... 607/119; 607/129; 607/130; 128/642
[58] Field of Search ...................................... 607/119, 122, 607/123, 126, 129, 130, 5, 6, 9, 48; 128/731, 733

[56] References Cited

U.S. PATENT DOCUMENTS

| | | | |
|---|---|---|---|
| 4,030,509 | 6/1977 | Heilman et al. | 607/4 |
| 4,136,702 | 1/1979 | Trabucco | 607/130 |
| 4,628,937 | 12/1986 | Hess et al. | 607/129 |
| 4,641,656 | 2/1987 | Smits | 607/129 |
| 4,969,463 | 11/1990 | Dahl et al. | 128/419 |
| 5,230,337 | 7/1993 | Dahl et al. | 607/5 |
| 5,327,909 | 7/1994 | Kiser et al. | 607/129 |
| 5,342,407 | 8/1994 | Dahl et al. | 607/129 |
| 5,360,442 | 11/1994 | Dahl et al. | 607/129 |
| 5,405,374 | 4/1995 | Stein | 607/122 |
| 5,425,364 | 6/1995 | Imran | 128/642 |
| 5,439,485 | 8/1995 | Mar et al. | 607/119 |
| 5,456,254 | 10/1995 | Pietroski et al. | 128/642 |

OTHER PUBLICATIONS

Knisley S, Davis C. "Membrane Polarization During Point Stimulation in Perfused Rabbit Hearts," Circulation 90; I-176:1994. (abstract).

Knisley S, Hill B, Ideker R, "Virtual Electrode Effects in Myocardial Fibers," Biophysical Journal 66;719–728: 1994.

Saypol J, Bradley R, "A Mechanism for Anisotropic Reentry in Electrically Active Tissue" Biomedical Engineering and Instrumentation Program, National Center for Research Resources, Nat'l Institute of Health, Bethesda, Maryland.

Wikswo J, Lin S, Abbas R, "Virtual Electrodes in Cardic Tissue: A Common Mechanism for Anodal and Cathodal Stimulation" Biophysical Journal 69:2195–2210: 1995.

Knisley S, "Transmembrane Voltage Changes During Unipolar Stimulation of Rabbit Ventricle" Div. of Cardiovascular Disease of the School of Medicine and Dept. of Biomedical Engineering, University of Alabama Birmingham, accepted Aug. 27, 1995.

Primary Examiner—Jennifer Bahr
Assistant Examiner—David M. Ruddy
Attorney, Agent, or Firm—Gifford, Krass, Groh, Sprinkle, Patmore, Anderson & Citkowski, P.C.

[57] ABSTRACT

An electrode terminal is described for delivering a stimulation pulse to the heart or other tissues containing a linear array of fibers. The electrode terminal is elongated and adapted for orientation in a direction parallel to the tissue fibers. The device of the present invention further includes a power source for electrically energizing the terminal such that the energization of the terminal reduces the nonuniformity of the transmembrane voltage change in the tissue proximate the electrode which is produced during the stimulation pulse. Nonuniform transmembrane voltage changes are associated with arrhythmic conditions. The linear electrode of the present invention can be used for cardiac pacing, defibrillation, and the termination of tachycardia.

11 Claims, 1 Drawing Sheet

LINE ELECTRODE ORIENTED RELATIVE TO FIBER DIRECTION

BACKGROUND OF THE INVENTION

I. Field of the Invention

The present invention relates generally to electrodes and, more particularly, to an electrode for delivering stimulation to the heart.

II. Description of the Prior Art

Extracellular electrical stimulation is commonly used in cardiac pacing and anti-arrhythmic electrical therapy such as defibrillation and cardioversion. The process of extracellular electrical stimulation is thought to involve first the induced changes in transmembrane potentials during the stimulation pulse and then activation of transmembrane voltage dependent ion channels, e.g. sodium channels that conduct inwardly directed current.

Effects of electrical stimulation of the heart, such as the production of an action potential, reentry, defibrillation, or cardioversion, are thought to result from changes in transmembrane ion channels, whose states depend on the transmembrane voltage produced during the stimulation. Currently, electrodes which are designed to produce a localized effect such as circular, point, and small electrodes which screw into the heart are commonly used to deliver stimulation pulses to the heart.

The transmembrane voltage change produced by and during a stimulation pulse ($\Delta V_m$) is thought to be responsible for the effects of stimulation by changing the states of transmembrane voltage-dependent ion channels that produce excitation or graded responses. The measurements have shown that $\Delta V_m$ at sites away from a unipolar point stimulation electrode in anisotropic myocardium is nonuniform, reversing sign on the axis parallel to myocardial fibers and not reversing sign on the axis perpendicular to the fibers. This nonuniformity has been defined in measurements in which the $\Delta V_m$ has one sign (+ or −) near the electrode, while in regions away from the electrode, $\Delta V_m$ has the opposite sign, if the region is parallel to myocardial fibers. It will not have opposite signs in regions perpendicular to myocardial fibers.

The nonuniform $\Delta V_m$ in the heart complicates effects of stimulation since it introduces spatial differences and possible interactions between oppositely polarized regions which may have different states of their transmembrane voltage-dependent ionic currents. This nonuniformity is a disadvantage because it is believed that nonuniform $\Delta V_m$ can influence and even cause arrhythmias of the heart. A further disadvantage of a unipolar point stimulation electrode is that a small electrode, due to its small contact area, can produce high current density that can damage tissue locally.

BRIEF DESCRIPTION OF THE PRESENT INVENTION

The present invention provides an electrode for delivering a stimulation pulse to heart or other tissue which overcomes all of the above-mentioned disadvantages of previously known devices.

In brief, the present invention comprises at least one elongated electrode terminal which is placed on the heart or other tissue. The electrode is adapted for orientation in a direction parallel to the fibers of the tissue.

The electrode terminal is attached to an electrical pulse generator, or some other means for electrically energizing the terminal, so that the energization of the terminal oriented in a direction parallel to the tissue fibers reduces the non-uniformity of the transmembrane voltage change in the tissue near the electrode which is produced during the stimulation pulse.

BRIEF DESCRIPTION OF THE DRAWINGS

A better understanding of the present invention will be had upon reference to the following detailed description, when read in conjunction with the accompanying drawings, wherein like reference characters refer to like parts throughout the several views, and in which.

DETAILED DESCRIPTION OF A PREFERRED EMBODIMENT OF THE PRESENT INVENTION

Figure 1:
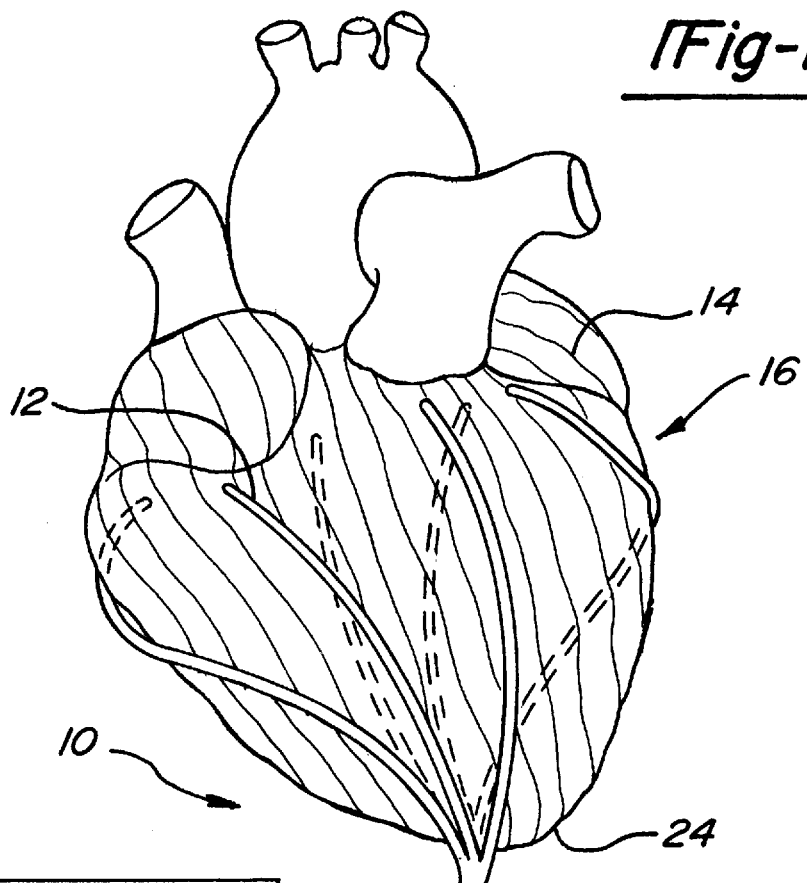
FIG. 1 is an environmental view of the device of the present invention.

With reference first to FIG. 1, an environmental view illustrating a preferred embodiment of the device 10 of the present invention is there shown and comprises at least one elongated electrode terminal 12, the terminal 12 being adapted for orientation in a direction parallel to the fibers 14 of the heart 16 or other tissue to be stimulated. Preferably, the electrode terminal 12 is long and thin, and made of a flexible, formable material which is capable of conducting a stimulation pulse to the heart 16 or other tissue. For applications pertaining to the heart 16, the electrode terminal 12 of the present invention may be inserted into the myocardium or may be positioned to contact the epicardium or endocardium. In a preferred embodiment, the electrode terminal 12 is slightly flexible so as to conform to the surface of the epicardium or endocardium, or to conform to changes in myocardial size or shape during contraction of the heart 16.

Figure 2:
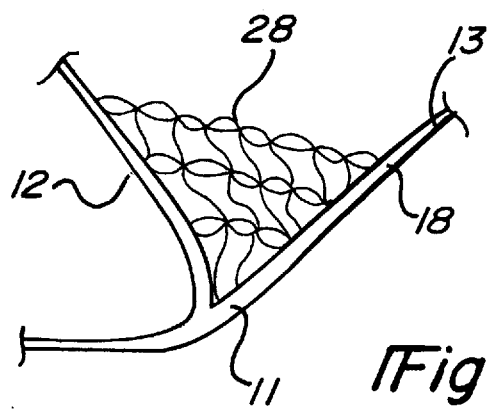
FIG. 2 is a view from the top of the electrode of the present invention.

As best shown in FIG. 2, the linear electrode 12 of the present invention can be made from a flat ribbon 18 of metallic material. The flat ribbon 18 is preformed so that when in place, the long axis of the electrode terminal 12 is parallel or approximately parallel to the myocardial fiber 14 direction of the myocardium adjacent to the electrode terminal 12.

Figure 3:
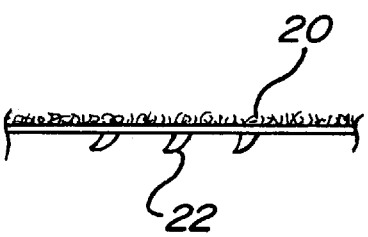
FIG. 3 is a view from the side of the electrode of the present invention.

In order to maintain constant electrical contact between the heart 16 tissue and the linear electrode terminal 12 throughout the length of the electrode terminal 12, the force per unit area normal to the heart 16 tissue must be constant. This can be accomplished in several ways. For example, as is shown in FIG. 2, the width of the linear electrode 12 can be gradually tapered from one end 11 to the other 13. Alternatively, as shown in FIG. 3, a nonconductive facing layer 20 can be adhered to one side of the linear electrode terminal 12, the stiffness of this facing layer decreasing from one end 11 of the electrode terminal 12 to the other 13. Other means of maintaining a constant electrical contact between the linear electrode 12 and the tissue can be used, as is known in the art. In areas where the width of the ribbon 18 is wider at one end 11 than at the other 13, a nonconductive coating (not shown) can be used to coat the edges of the wider end 11 so that the electrically active area of the electrode 12 contacting the heart 16 remains the same from one end 11 of the electrode 12 to the other 13.

The linear electrode of the present invention can be attached in or on the heart 16 or other tissue by means of conventional attachment means such as sutures or surgical staples. Alternatively, as best shown in FIG. 3, one or more hooks or tines 22 may protrude from one side of the linear electrode 12 in order to hold it in place. In order to facilitate insertion of the electrode, the hooks or tines can be coated with a smooth, biodegradable cap (not shown) which would prevent the tines 22 from gripping tissue prior to insertion, but would allow the tines 22 to grip the tissue once the electrode 12 was in place. In a preferred embodiment of the invention, the ends of the electrode terminal 12 have a greater resistance than the portion in between, so that the resistance near the ends of the terminal 12 increases gradually instead of increasing abruptly at the ends of the terminal 12. This will lessen nonuniformities of transmembrane voltage changes at the ends of the terminal 12, and will lessen what has come to be known as "the edge effect".

As best shown in FIG. 1, the device of the present invention may be comprised of a plurality of linear electrodes 12 joined at one end to a lead assembly 25 at the apex 24 of the heart 16. The lead assembly 25 is connected to an electrical pulse generator 26. A single lead assembly 25 may connect all electrodes 12 to the electrical pulse generator, as is shown in FIG. 1. However, in an alternate embodiment (not shown) one or more lead assemblies 25 can be used to connect any one, pair, or combination of linear electrodes 12 to the pulse generator 26. This type of joining method allows for many variations in electrical pulse application such as polarity, timing, and/or waveform shape. As best shown in FIG. 2, if a plurality of linear electrodes 12 is utilized, each electrode 12 may be laterally positioned with respect to the adjacent electrode 12 by means of electrically insulated webbing or netting material 28 which will form a "sock" around the heart 16. This would also help to keep the plurality of electrodes 12 in place.

From the foregoing, it can be seen that the present invention provides a novel means for producing a uniform direction of the transmembrane voltage change in a large region of tissue, either depolarization for cathodal extracellular stimulation or hyperpolarization for anodal extracellular stimulation. A further advantage of the present invention is that a linear electrode 12 will provide greater surface area and thus less current density and tissue damage near the electrode 12 due to current density. Unlike previously known circular or point electrode terminals, the present invention of an electrode terminal 12 in or around the heart 16 parallel with the fiber 14 direction produces an effect in recovered or relatively refractory tissue that is more controlled or more predictable than previously known electrodes. The linear electrode terminal 12 of the present invention may be used in heart applications for cardiac pacing, defibrillation, and the termination of ventricular tachycardia, as well as with an atrial stimulation scheme including pacing or the termination of atrial fibrillation, flutter, or tachycardia. The present invention may also be used to stimulate all other biological tissues made up of a linear array of fibers and which are capable of being affected by electrical stimulation, such as neural and muscular stimulation.

Having described my invention, however, many modifications thereto will become apparent to those skilled in the art to which it pertains without deviation from the spirit of the invention as defined by the scope of the appended claims.

I claim:

1. A device for delivering a stimulation pulse to an elongated fiber forming a tissue of a patient, said device comprising:

at least one elongated electrode terminal having a first end and a second end, and a portion therebetween, said terminal adapted for orientation in a direction parallel to said fiber of said tissue which is adjacent to said terminal from said first end to said second end of said terminal, said electrode terminal further comprising a nonconductive facing layer attached to one side of said terminal, said facing layer comprised of a material of decreasing stiffness from said first end to said second end of said terminal, and means for electrically energizing said terminal, whereby the energization of said terminal reduces the nonuniformity of the transmembrane voltage change in the tissue proximate said electrode produced during said stimulation pulse.

2. The invention as defined in claim 1 wherein said electrode terminal is uninsulated.

3. The invention as defined in claim 1 wherein said electrode terminal is flexible.

4. The invention as defined in claim 1 wherein said first and second ends of said terminal have a greater resistance than said portion therebetween.

5. The invention as defined in claim 1 wherein said electrode terminal is flat.

6. The invention as defined in claim 1 wherein said electrode terminal is preformed so as to lie parallel to said fiber of said tissue which is adjacent to said terminal.

7. The invention as defined in claim 5 wherein said electrode terminal tapers from said first end to said second end of said terminal.

8. The invention as defined in claim 1 wherein said electrode terminal further comprises at least one tine protruding outwardly from said electrode.

9. The invention as defined in claim 1 and further comprising at least two electrodes laterally interconnected with insulated webbing therebetween.

10. A method for delivering a stimulation pulse to an elongated fiber forming a tissue of a patient, said method comprising the steps of:

providing an elongated electrode terminal, said terminal having a first end and a second end, and a portion therebetween, orienting said terminal in a direction parallel to said fiber which is adjacent to said electrode terminal from said first end to said second end of said terminal, electrically energizing said terminal, whereby the energization of said terminal reduces the nonuniformity of the transmembrane voltage change in the tissue proximate said electrode produced during said stimulation pulse.

11. A method for delivering a stimulation pulse to an elongated tissue fiber, said method comprising the steps of:

providing a plurality of elongated electrode terminals, each of said terminals having a first end and a second end, and a portion therebetween, said electrode terminals being independently positionable with respect to each other, orienting at least one said electrode terminal in a direction parallel to one of said elongated tissue fibers which is adjacent said electrode terminal from said first end to said second end of said terminal, electrically energizing said terminals, whereby the energization of each said terminal reduces the nonuniformity of the transmembrane voltage change in the tissue proximate to said electrode terminal producing said stimulation pulse.

* * * * *

UNITED STATES PATENT AND TRADEMARK OFFICE
CERTIFICATE OF CORRRECTION

PATENT NO. : 5,824,028
DATED : October 20, 1998
INVENTOR(S) : Stephen B. Knisley It is certified that error appears in the above-identified patent and that said Letters Patent is hereby corrected as shown below:

Title page, item [56] insert the following:

U. S. PATENT DOCUMENTS

| EXAMINER INITIAL | | PATENT NUMBER | | | | | | ISSUE DATE | PATENTEE | CLASS | SUBCLASS | FILING DATE IF APPROPRIATE |
|---|---|---|---|---|---|---|---|---|---|---|---|---|
| | | 4 | 5 | 7 | 4 | 8 | 1 | 4 | 3/86 | Buffet | 128 | 786 | 07/08/82 |
| | | 4 | 7 | 0 | 8 | 1 | 4 | 5 | 11/87 | Tacker Jr. et al | 128 | 419 | 09/11/85 |
| | | 5 | 0 | 1 | 0 | 8 | 9 | 4 | 4/91 | Edhag | 128 | 75 | 01/09/89 |
| | | 5 | 0 | 5 | 0 | 6 | 0 | 1 | 9/91 | Kupersmith et al. | 128 | 419 | 05/29/90 |
| | | 5 | 1 | 0 | 3 | 8 | 2 | 2 | 4/92 | Duncan | 128 | 419 | 04/03/90 |
| | | 5 | 1 | 8 | 1 | 5 | 1 | 1 | 1/93 | Nickolls et al. | 128 | 419 | 10/21/91 |
| | | 5 | 2 | 8 | 2 | 8 | 4 | 5 | 2/94 | Bush et al. | 607 | 128 | 10/01/90 |
| | | 5 | 4 | 1 | 1 | 5 | 2 | 7 | 5/95 | Alt | 607 | 5 | 08/31/92 |
| | | 5 | 4 | 2 | 3 | 8 | 6 | 4 | 6/95 | Ljungstroem | 607 | 5 | 12/02/93 |
| | | 5 | 4 | 3 | 3 | 7 | 2 | 9 | 7/95 | Adams et al. | 607 | 5 | 03/24/92 |
| | | 5 | 4 | 8 | 9 | 2 | 9 | 3 | 2/96 | Pless et al. | 607 | 5 | 03/31/94 |

OTHER DOCUMENTS(Including Author, Title, Date, Relevant Pages, Place of Publication*)

Knisley S., Grant A., "Asymmetrical Electrically Induced Injury of Rabbit Ventricular Myocytes", J Mol Cell Cardiol 27, 1111-22(1995).

Knisley S., Smith W., Ideker R., "Prolongation and Shortening of Actual Potentials By Electrical Shocks in Frog Ventricular Muscle", Am.J. Physiol. 266(Heart Circ. Physiol. 35) H2348-H2358, 1994.

Signed and Sealed this

Twenty-fifth Day of July, 2000

Attest:

Attesting Officer

Q. TODD DICKINSON

Director of Patents and Trademarks

UNITED STATES PATENT AND TRADEMARK OFFICE
CERTIFICATE OF CORRECTION

PATENT NO. : 5,824,028
DATED : October 20, 1998
INVENTOR(S) : Stephen B. Knisley It is certified that error appears in the above-identified patent and that said Letters Patent is hereby corrected as shown below:

Column 1,
Line 4, insert:

-- GRANT REFERENCE

The subject invention was made with government support under a grant from the National Institutes of Health, Grant Nos. RR11718 and HL52003. The government has certain rights in the invention. --.

Signed and Sealed this

Twenty-fourth Day of January, 2006

JON W. DUDAS
*Director of the United States Patent and Trademark Office*